(12) United States Patent
Rosen

(10) Patent No.: US 8,146,449 B2
(45) Date of Patent: Apr. 3, 2012

(54) DEVICE AND METHOD FOR NONDESTRUCTIVE TESTING OF PIPELINES

(75) Inventor: Hermann Rosen, Kastanienbaum (CH)

(73) Assignee: Rosen Swiss AG, Stans (CH)

( * ) Notice: Subject to any disclaimer, the term of this patent is extended or adjusted under 35 U.S.C. 154(b) by 609 days.

(21) Appl. No.: 12/324,922

(22) Filed: Nov. 28, 2008

(65) Prior Publication Data

US 2009/0293622 A1    Dec. 3, 2009

(30) Foreign Application Priority Data

Nov. 30, 2007   (DE) .......................... 10 2007 058 043

(51) Int. Cl.
*G01N 17/00*   (2006.01)
(52) U.S. Cl. ....................................................... 73/865.8
(58) Field of Classification Search .................... 73/623, 73/865.8
See application file for complete search history.

(56) References Cited

U.S. PATENT DOCUMENTS 5,565,633 A * 10/1996 Wernicke ..................... 73/865.8

* cited by examiner

*Primary Examiner* — Hezron E Williams
*Assistant Examiner* — Tamiko Bellamy
(74) *Attorney, Agent, or Firm* — Gudrun E. Huckett

(57) ABSTRACT

A device for nondestructive testing of pipelines is designed to move along a pipeline and has at least one measuring unit for acquiring measured data of the pipeline, wherein the device is self-propelled and has at least one functional unit rotatable about a central axis of the device for acquiring measured data and/or for driving the device. In a corresponding method for nondestructive testing of pipelines, the device is moved along the pipeline by a functional unit having drive elements and moving helically along a surface of the pipeline to be covered. The functional unit acquires measured data and the drive elements are forced by a magnetic field generated by the functional unit against the surface of the pipeline.

18 Claims, 5 Drawing Sheets

DEVICE AND METHOD FOR NONDESTRUCTIVE TESTING OF PIPELINES

BACKGROUND OF THE INVENTION

The invention concerns a device for nondestructive testing of pipelines wherein the device is designed for moving along a pipeline and comprises at least one measuring unit for acquiring measured data of the pipeline. Moreover, the invention concerns a method for nondestructive testing of pipelines.

Devices of the aforementioned kind serve for monitoring pipelines with regard to inhomogeneities, for example, metal loss at the pipe wall, corrosion or cracks. In this connection, known devices are guided across dozens of kilometers along the outer side or inner side of the pipelines. The measured data obtained by various nondestructive examination methods cover the surface to be measured completely. Known devices of the aforementioned kind have at the side facing the surface to be measured continuous measuring units, i.e., measuring units that cover the circumference of the pipeline completely. As a result of the plurality of measuring units such system are generally very heavy.

It is an object of the present invention to improve a device in such a way that it moves in an improved way along a pipeline. Also, a method for nondestructive testing of pipelines is to be improved.

SUMMARY OF THE INVENTION

The object is solved by a device according to the invention that is of a self-propelled and has at least one functional unit that is rotatable about a center axis of the device for acquiring the data and/or for driving the device.

The functional unit is located at a lateral face of the device that is facing the surface of the pipeline to be measured. Preferably, the device is used for being passed through pipes and the functional unit is arranged at the outer side of the device. However, it is also conceivable to guide the device along the exterior of a pipe. By rotation of the at least one functional unit designed for acquiring measured data, a complete coverage of the surface to be assayed is achieved. It is not necessary to provide across the outer side or inner side of the device continuous functional units, i.e., functional units that completely cover the surface to be assayed. The term continuous assaying is to be understood as assaying within the bounds of the possible resolution precision, i.e., also a quasi-continuous resolution.

It is possible to forego a plurality of devices for acquiring measured data. The device is more lightweight. It can be designed to be self-propelled, i.e., can be provided with its own drive system. As a result of the minimal weight the energy loss caused by friction is only minimal. The energy required for advancement can be carried onboard.

The functional unit assays only a circumferential area and defines by rotation during its movement along the pipeline a helical strip. This strip covers the area to be assayed completely and can be optionally configured so as to be overlapping.

In one embodiment of the invention with at least one functional unit rotating about an axis, the functional unit is designed for driving the device and moves along a helical path. By means of the rotation of the functional unit, representing a drive unit, along the outer side or inner side of the device, the force that can be utilized for advancing and that is generated by the drive unit is geared down. Even heavier devices can be moved easily. As a result of the own weight of the preferably externally positioned drive units a more stable system is obtained and by means of the externally positioned drive action also a rotational movement that is neutral with respect to counter torque is provided. Both can improve the precision of the measurements.

Especially advantageous is the configuration of the functional unit for acquiring measured data and for driving the device. The disadvantage of the functional unit traveling an additional distance along the pipeline as a result of the helical shape is compensated by the advantages, in particular because of the energy savings as a result of the reduced weight. The functional unit can be of a compact configuration, for example, provided with small electric motors for the drive action, so that even more space is available for energy storage. The control of the device and the evaluation of the measured data is improved by combination of drive and at least partial measurement in one functional unit. The distance traveled by the drive and the acquired measured data are directly interdependent.

Advantageously, the device has a plurality of functional units, preferably between 2 to 5, wherein the device is configured to provide complete pipe wall coverage by means of combination of the strips assayed by the functional units during their rotation and their advancing movement along the pipeline. Each functional unit covers only a circumferential section or partial section of the circumference. This section that is, for example, located on a cylinder wall surface and is detected by the functional units provides a complete coverage of the pipe wall to be measured only upon rotation and combination of the individual helical strips upon advancing movement of the device. At the same time, smaller drive units arranged on the individual functional units can provide satisfactory advancing action.

Preferably, the device has three functional units that are arranged substantially along a plane transverse to a center axis of the device. By means of this number of functional units an excellent ratio of coverage of the surface to be assayed to the weight of these units is provided.

For traveling through or externally along a pipeline, it is advantageous to arrange the functional unit on a frame that is adjustable in a direction along a line that is perpendicular to the central axis of the device. In this way, the device can be adjusted in a simple way to changes of the pipeline diameter, bulges (oval sections) or the like. In a combination of a drive and a measuring unit in one functional unit, these two can together travel across the depressions and bulges so that the measured results are even more precise. Preferably, for an active control of this movement the device has an electromechanical distance regulation that by means of suitable sensors and control units controls the distance of the functional units from the surface to be assayed. Between functional unit and pipe wall a uniform air gap, for example, 1-2 mm, is always maintained.

The term assaying of the surface means sensing across the entire area of the surface or the pipeline. In this connection, this can mean also acquiring measured data, for example, across the entire thickness of the pipeline wall and transversely through the wall to the (outer or inner) side.

In a further advantageous embodiment of the invention the functional unit can be rotated, preferably in a controlled fashion, about an axis that is perpendicular to the center axis of the device. The functional units can be adjusted, for example, to provide partial overlap of the individual helical strips before the measuring ride begins. For regulation based on predeterminable criteria, the functional units can preferably be designed so as to be rotatable during a measuring travel in a controlled fashion. For example, adjusting means are advantageous that operate by a motor or optionally also based on magnetism so as to enable, for example, a faster advancement or a greater overlap for generating redundant measured values/data.

While, in accordance with one inventive embodiment, the device can be driven by means of the functional unit by electromagnetic interaction with a ferromagnetic pipeline wall, according to a further preferred or additional embodiment of the invention the functional unit is provided with a drive unit whose drive means can be positioned at an angle of incidence to a plane extending perpendicularly through the central axis of the device. The drive means can be rotated, for example, about the afore described perpendicular axis relative to the center plane of the vehicle.

It is especially preferred that the functional unit has drive means that are embodied as wheels that are electromotively operated. They can be supplied with energy, for example, by means of sliding contacts from other non-rotating parts of the device. By means of the angle of incidence of the wheels the coverage or overlap of the pipe wall is changed with the goal to either generate partially redundant measured data or to effect a faster advancement of the device through the pipeline.

Advantageously, the device is provided with a functional unit that generates a partial magnetic field, i.e., a magnetic field that in the circumferential direction at a point in time generates an incomplete magnetic field. The power required simultaneously for generating the magnetic fields is reduced.

According to a further embodiment of the invention the drive means are designed to be forced against the pipe wall by means of magnetic interaction with the pipe wall. In this connection, the drive means can be designed, for example, as magnetic drive wheels and optionally can realize the afore described partial magnetization or can be designed to be attracted by a magnetized pipe wall.

Especially advantageous is however the configuration of a functional unit in such a way that the drive means, secured by means of magnetic interaction, are designed to be supported on the base. In interaction with the pipe wall by means of its magnetization through the functional unit an attractive force is produced that forces the drive means of the (drive) functional unit against the pipe wall. Therefore, a pressing device is not needed. This provides significant savings in regard to weight.

The device can be secured, for example, by means of permanent magnets magnetically on the pipe wall. In such an embodiment of the present invention, no friction is acting and the individual device parts that are in contact with the pipeline will wear less.

At the same time, by generating the magnetic field, a working step can be realized already that is required for acquiring the measured data in a plurality of methods. The functional units each represent in this connection a measuring and drive device that in particular with the afore described advantages of further features of the device according to the invention can be used in an excellent way for a plurality of pipelines to be tested.

The magnetization of the pipeline wall is realized at a spacing to the wall. This provides high attractive forces and therefore high contact forces for the drive means. The functional units can move the device at high tractive power. A further increase of the tractive power is realized by the geared down transmission of the force generated by the drive wheels by means of the helical movement along the pipeline wall.

A device according to the invention can be designed, preferably by appropriate configuration of the functional units, for acquiring measured values by means of magnetic flux leakage (MFL) methods, electromagnetic acoustic transducer (EMAT) methods, eddy current (EC) methods, and/or ultrasound (UT) methods. Magnetic field sensors entrained along the pipe surface detect in this connection changes of the magnetic flux (in particular direction and strength) so that inhomogeneities, for example, metal loss on the pipe wall, can be detected. By means of electroacoustic sensors metal loss, cracks in the inner and outer sides of the pipe wall as well as damage to the envelope on the outer side of the pipe can be detected while eddy current sensors serve for recognizing metal losses of smaller size that appear on the inner side of the pipe wall. By means of ultrasound sensors it is possible to detect, for example, metal loss on the inner side and outer side and other inhomogeneities in pipelines that are filled with liquid.

However, these individual measuring and sensing units of the functional units can be of different design, respectively. For example, in case of a total of four measuring units it is possible to provide two MFL measuring units and two EMAT units wherein the areas that are covered by the identical measuring units in combination cover the entire surface area to be tested.

A device according to the invention, configured to generate partial magnetization of the pipe wall by means of individual rotating (multi) functional units by means of e.g. a magnetic yoke correlated with each functional unit, makes possible a lightweight construction of the entire device and enables inspection of very large pipe diameters while providing high flexibility. Along the circumference of the device and of a pipe section perpendicular to the axis of the pipe the excitation area of the measuring unit is not continuously distributed in this connection.

Moreover, it is advantageous for an inventive device to have at least part of the device configured as a non-rotating tender, i.e., as an entrained transport and supply unit. Such a transport unit can be supported on the pipe wall, for example, by means of wheels. Between the rotating part of the device that comprises the functional unit(s) and the tender, a rotary joint is provided for this purpose that, for example, connects the frames of the individual units with one another.

For further assisting the movement along pipeline, the tender is preferably provided with at least one directional means that counteracts rotational movement. A tender can be used as a supply unit for energy supply and, for example, can comprise an electric generator that is powered by diesel fuel or regular fuel and that, by means of sliding contacts, is connected to the functional units.

Moreover, the device, in particular a tender can have spring force-loaded support elements. They can be embodied as lever arms that by means of frame parts that contract in the direction of a central axis of the device are forced outwardly/inwardly or inwardly.

According to a further embodiment of the device according to the invention, the device is provided with a failsafe system that in case of a functional failure removes, for example, the functional units from the pipeline wall and, for example, by means of auxiliary drives, provides exclusively a drive action toward a service station. Support wheels can be folded against the pipe wall and, in addition, the magnetic attraction that may still be present can be canceled by switching the magnetic poles.

Alternatively or additionally, the device can have a folding sealing sleeve that upon unfolding in an emergency situation provides a sealing action for a pipeline cross-section and enables the device located in the pipeline to be moved out by means of a conveying action provided by a medium.

For communication with the device by means of in particular bidirectional low-frequency signals, the device is configured preferably with a corresponding communication device. Low-frequency signals have been found to be particularly suitable for pipelines.

It is understood that the device according to the invention that is designed as a self-propelled vehicle, i.e. has its own drive, can also be provided with its own control unit. The control unit can determine, for example, during a measuring ride whether a measurement is to be repeated, for example, because of a sensor failure. This can be realized then by changing the angle of incidence of the functional unit or by moving back and forth within the pipeline.

The object is furthermore solved by a method for nondestructive testing of a pipeline wherein the measured data that have been acquired by means of the device moved along the pipeline completely cover the pipeline. In this connection, the device moves along the pipeline by means of a functional unit that moves helically along the surface to be covered wherein the functional unit provided for this purpose with drive means acquires measured values and wherein, by means of a magnetic field generated by the functional unit, the drive means are forced against the surface of the pipeline. The method according to the invention enables that the device can be moved with high precision and in an intelligent way and in a self-controlled fashion through a pipeline.

BRIEF DESCRIPTION OF THE DRAWINGS

Further advantages and details of the invention result from the Figures described in the following.

DESCRIPTION OF PREFERRED EMBODIMENTS

Figure 1:
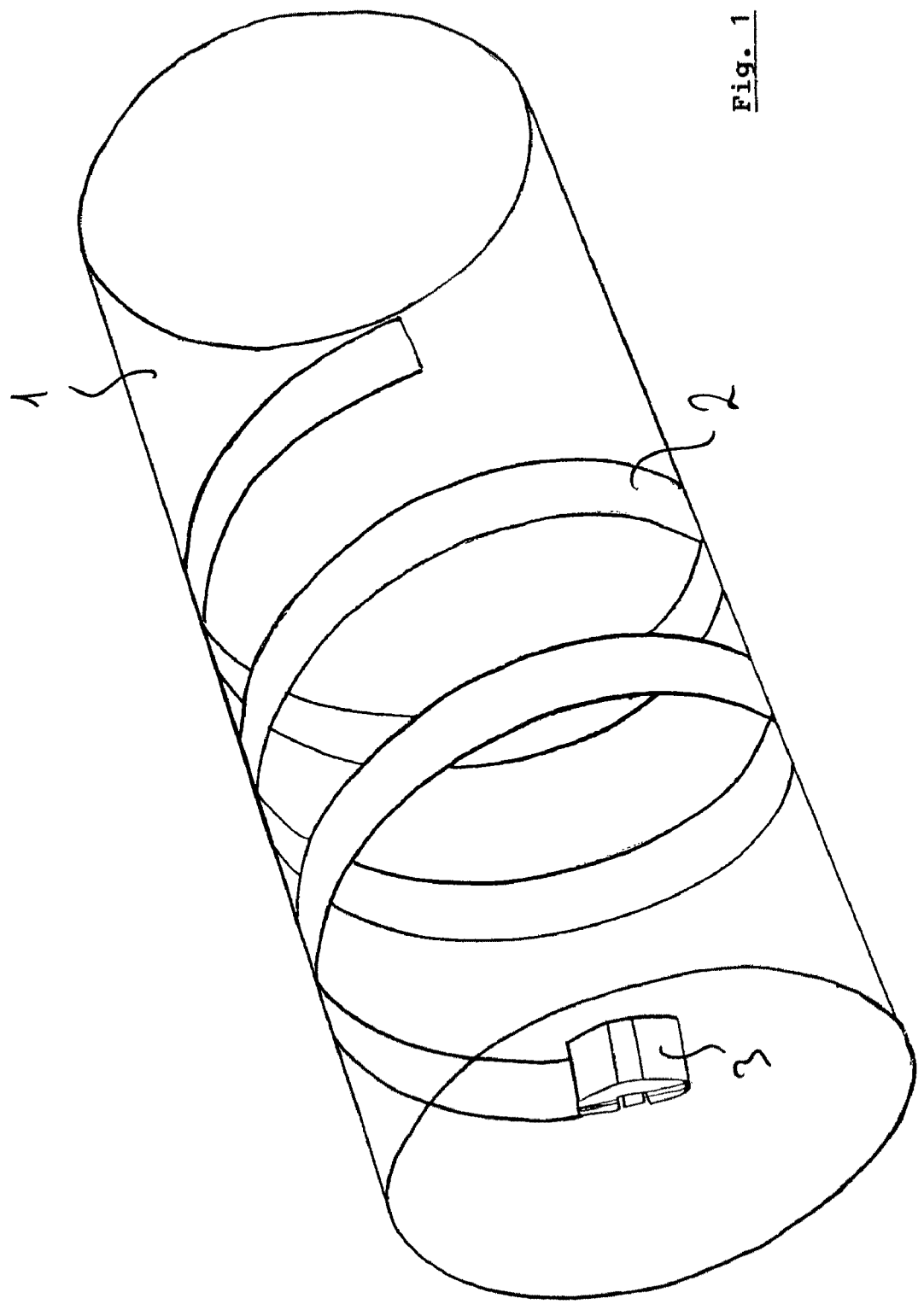
FIG. 1 shows the measured area covered by the device according to the invention.

Individual technical features of the objects described in the following can be the subject matter of the invention when used alone, in combination with the already afore described features and/or combined with one another and can provide advantages within the context of the invention. Identical or similarly functioning parts of the devices are identified with identical reference numerals, should this be beneficial.

FIG. 1 shows a pipeline 1 to be tested. By rotation of a functional unit and simultaneous advancing movement of the device through the pipeline 1 a helical strip is generated by means of a measuring or analytical unit 3. This helical strip corresponds to the area of the surface of the inner side of the pipe which area is covered by the measuring unit 3 during its movement.

By combination of three functional units of the device (not illustrated) each comprising a measuring unit 3 that is embodied in the illustrated embodiment as a MFL unit, the inner wall 4 of the pipeline is completely covered. The device, despite the fact that the functional units cover individually only parts of the pipe, acquires a complete image of the pipe with only three measuring units in a plane that is perpendicular to the pipeline axis.

Figure 2:
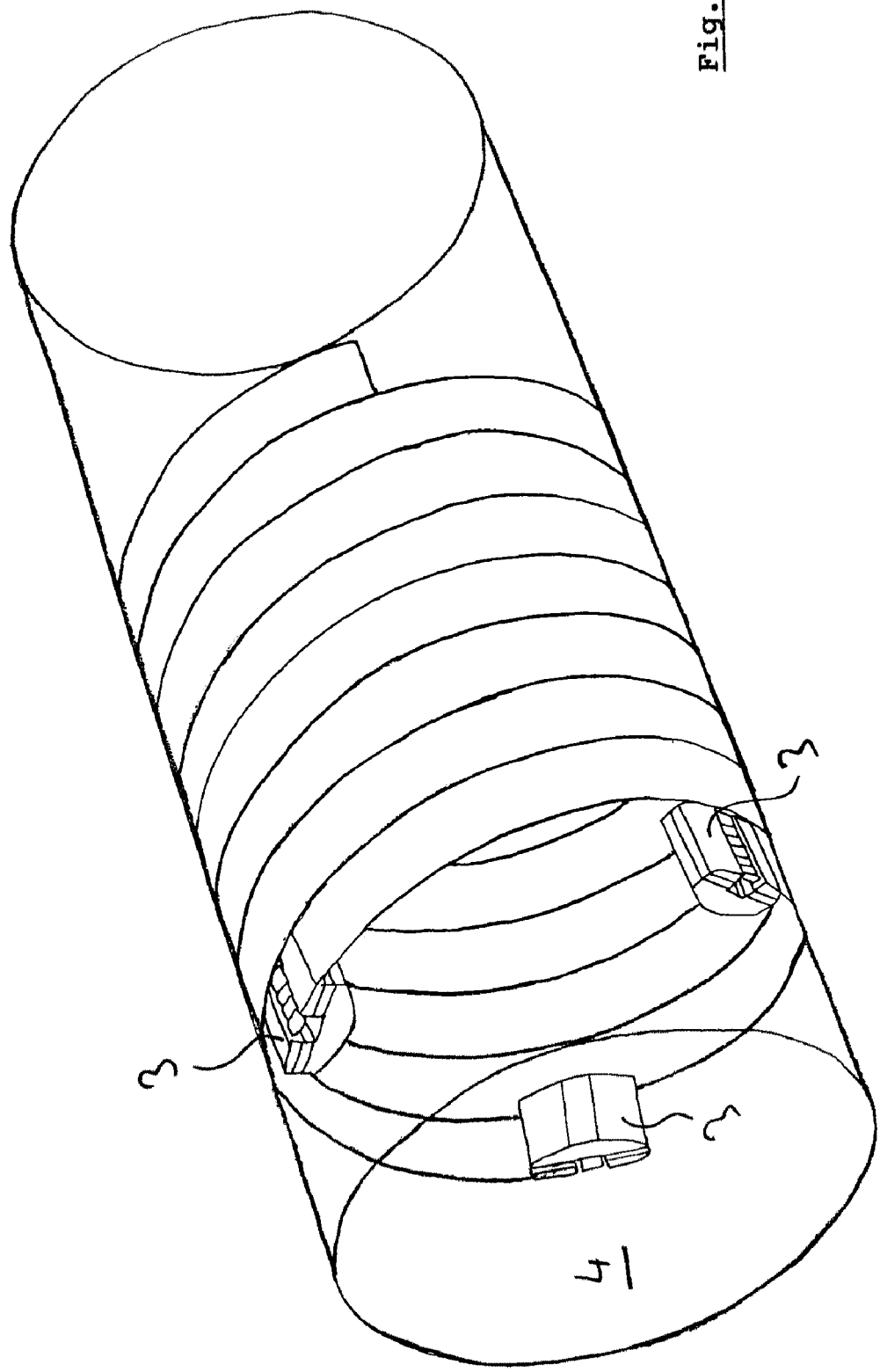
FIG. 2 shows the inner wall section of the pipe that is completely covered by the device according to the invention provided with three functional units.

With the aid of FIG. 2 it can furthermore be seen that for a slower advance at unchanged rotational speed of the measuring units 3, a stronger overlap of the strips would occur so that redundant measuring results can be produced. This increases the reliability of the acquired measured data. For example, such a greater overlap can be effected by a less strong pivoting of the drive means correlated with a measuring unit 3 in the direction of a center axis of the pipeline.

The measuring units 3 generate a magnetic field by means of which the entire functional unit with its drive means is pressed against the inner side 4 of the pipeline. A pressing device can thus be eliminated. When looking at FIGS. 1 and 2, it is already apparent that a device according to the invention is of a significantly lighter design because of the significantly reduced number of measuring units 3 that generate a great portion of the weight of conventional devices. This has advantages not only for the energy consumption required for movement but also entails a reduced risk of damage for the pipelines to be tested.

Figure 3:
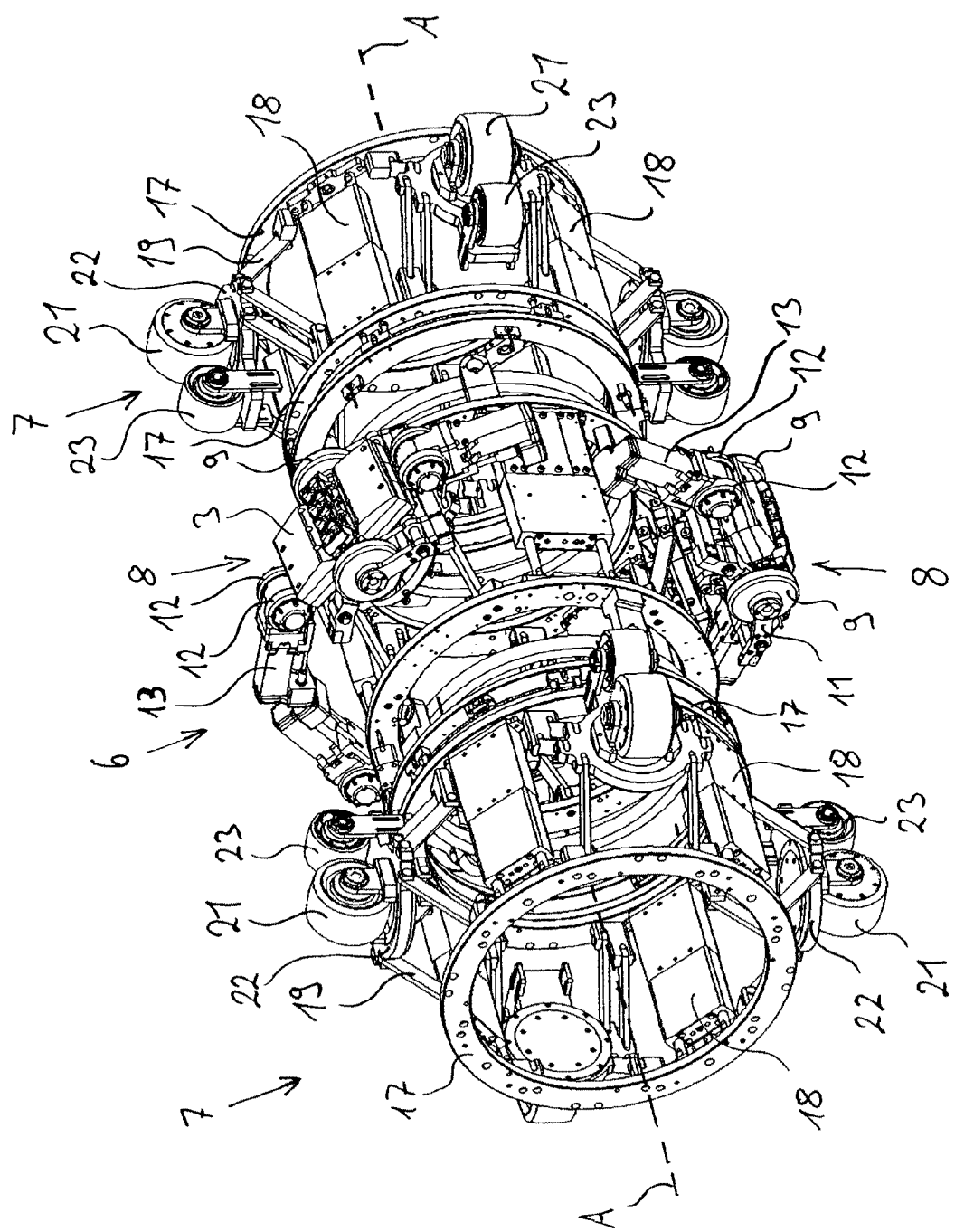
FIG. 3 is a partial illustration of a device according to the invention.

In FIG. 3, a device according to the invention is schematically shown. According to the embodiment, the device is of a three-part configuration with a rotating central part 6 and tenders 7 arranged in the direction along a center axis A of the device before and behind the center part. The device has three functional units 8 that are uniformly and discretely distributed about the circumference (compare FIG. 3 and FIG. 4). Each functional unit 8 comprises a MFL unit as a measuring unit 3. The measuring units are delimited laterally by a wheel 9, respectively. The wheels 9 are rigidly arranged by means of an arm 11 on the functional unit 8 and serve for maintaining a minimum distance of the measuring unit from the pipe wall or the inner side 4 of the pipeline. By means of the magnetic field generated by the MFL unit an attractive force is generated that is oriented in the direction toward the surface of the pipeline wall to be measured. By means of this attractive force the four drive wheels 12 of each functional unit 8 are pressed against the inner side 4 of the pipeline.

The drive of the wheels 12 is realized by means of electric motors 13 that are each supplied by non-illustrated supply units, e.g. in the form of accumulators or generators, with energy. The supply units are preferably arranged in the tenders 7.

By slanted positioning of the functional units 8 that are rotatable about an axis 24 positioned perpendicularly to the center axis A of the device, the wheels 9 directly arranged on the measuring unit as well as the wheels 12 of the drive unit are positioned at an angle relative to a perpendicular plane that is perpendicular to the center axis of the device. The functional units 8 are moved by the wheels 12 in the pipe along a helical curve 2 about the inner side 4 of the pipe. In this way, the strip-shaped areas in FIG. 2 are generated that cover the pipe 1 completely.

The screw-shaped or helical advancing movement of the functional units 8 provided on the outer side of the device on a frame that is correlated with the central part 6 causes a rotation of the frame about the center axis A of the device. The frame is driven by means of the outer functional units so as to be neutral with regard to counter torque. The spiral movement of the drive wheels 12 effects a geared down transmission ratio for the movement along the center axis of the pipeline 1 that is parallel to the center axis A of the device. This leads to a reduction of the speed along the aforementioned axis A but to an additional gain in tractive force. The tenders 7, arranged on the rotating central part 6 and provided preferably with communication, control and energy supply devices, can be entrained without problems. The tenders 7 are connected by a universal joint 14 with the center part 6. The central part 6 rotates together with the universal joints relative to the tenders 7 that are stationary relative to the pipeline wherein the connection has additionally a bearing 16 adjacent to the universal joints 14 for this purpose. The individual parts of the device are torque-decoupled relative to the rotation of the central part 6 effected by the functional units.

Each tender 7 has two disk-shaped frame parts 17 that are connected to one another by contracting spring packs 18 provided with a guide. The contraction of the spring packs 18 causes in connection with the lever arms 19 correlated with a frame part 17, respectively, an erection and thus support of the guide means embodied as guide wheels 21 on the inner side 4 of the pipeline. The wheels 21 are forced with a contact pressure adjustable by the spring packs 18 against the inner wall of the pipeline and ensure additionally that the tenders 7 are not rotated together with the central part 6. The wheels 21 are arranged so as to be rotatable on a controllable bearing 22. On this bearing 22 lever arms engage and the wheels 21 are forced outwardly. Inasmuch as by means of appropriate sensors a beginning rotation of the tenders 7 is determined, by means of a control unit of the bearings 22 this rotational movement can be counteracted.

Each bearing 22 has further guide rollers 23 correlated therewith that, in combination with the guide wheels 22, contribute to the stabilization of the tenders 7 in the direction of the longitudinal axis A.

Figure 4:
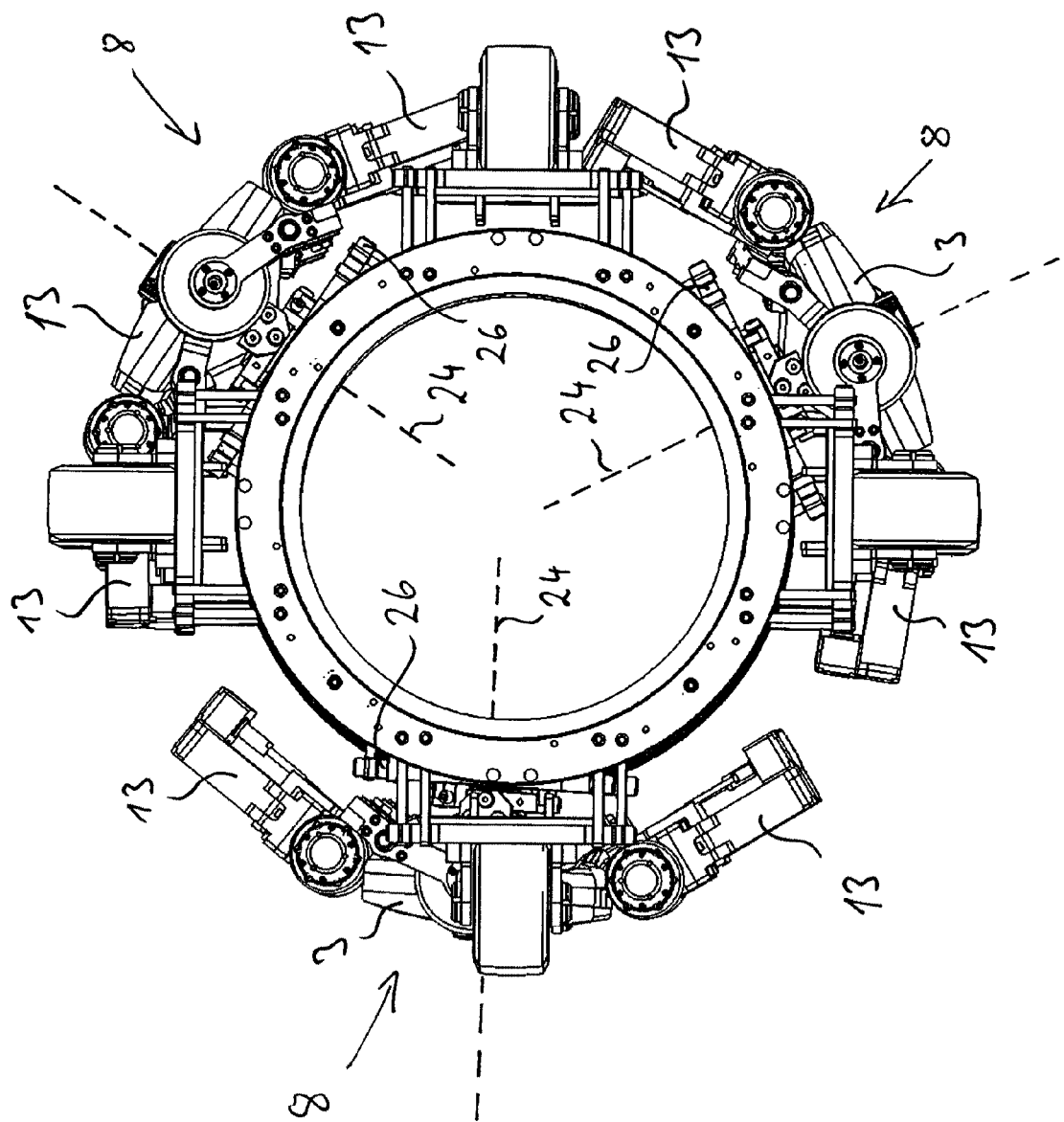
FIG. 4 shows the object of FIG. 3 in a front view.
Figure 5:
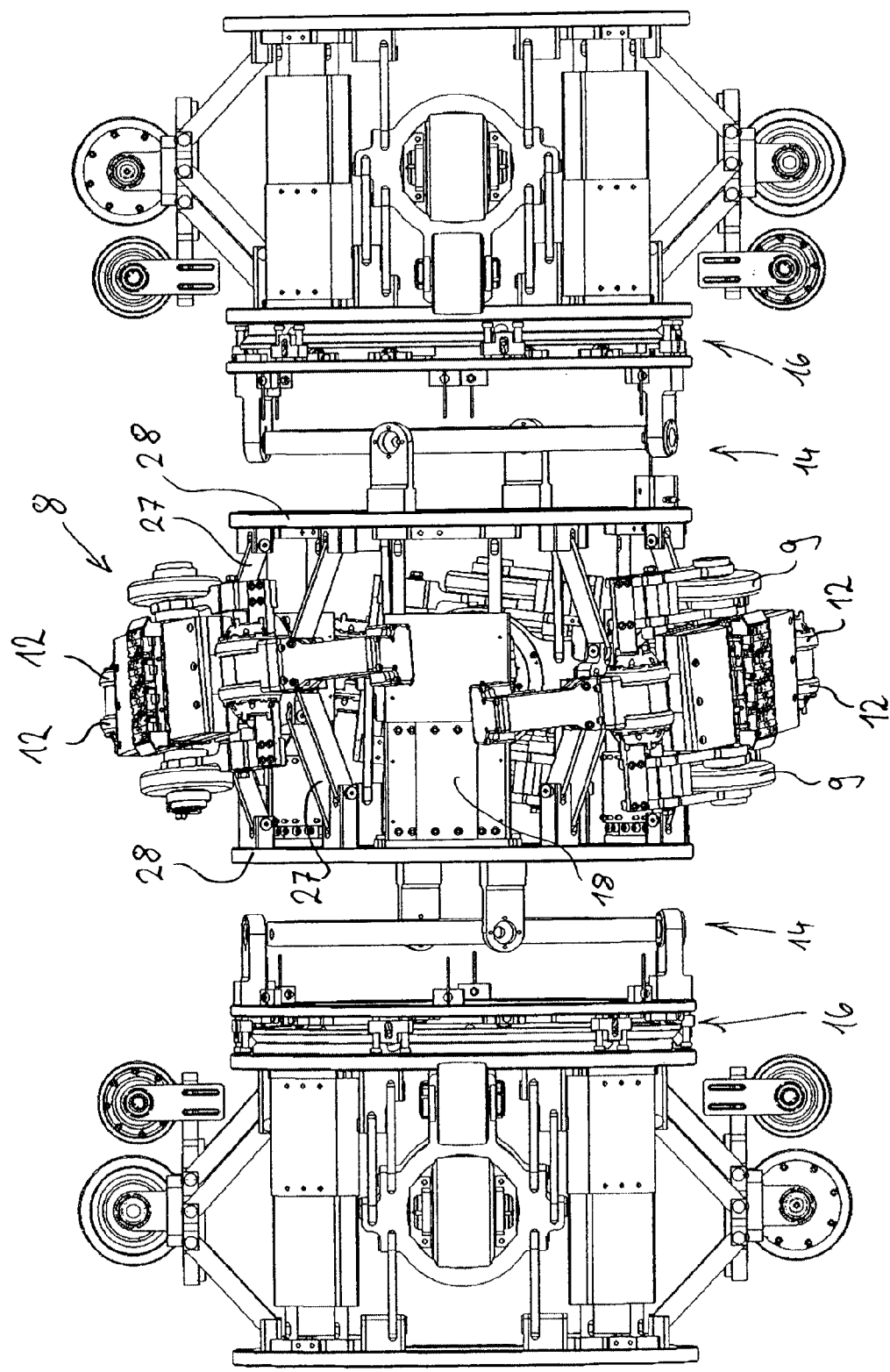
FIG. 5 shows the object of FIG. 3 in a side view.

The discrete distribution of functional units 8 about the circumference of the device can be seen particularly well in FIG. 4. The three measuring units 3 are uniformly distributed about the circumference. The same holds true for the drive wheels 12 that are driven by the electric motors 13. The functional units 8 that are rotatable about axes 24 are also supported in adjustable bearings 26. By means of these adjustable bearings the angle of incidence of the wheels 12 and thus the overlap or the advancement of the device through the pipeline can be varied.

The orientation of the measuring units and of the electric motors is realized such that the inner side 4 of the pipe is filled out in the way of a quasi envelope. The support of the functional units 8 by rotary bearings 26 creates an adjustability of the incline of the helical strips 2 along the pipeline 1. With a corresponding programming of a control unit, not illustrated, or by means of intervention during a measuring ride of the device through a pipeline, the advancement of the device can be varied by means of these adjustable rotary bearings 26.

The individual functional units 8 are movably supported by lever arms 27 on the frame parts 28 that form the basic frame of the central part 6. By means of spring packs 18, through the lever arms 27 arranged on the rotary bearings 26 a pre-adjustment of the diameter of the central part is effected. However, in this way, no contact pressure or only an insignificant contact pressure of the drive wheels 12 is exerted onto the surrounding inner wall 4 of the pipeline. The spring packs 18 thus do not impair the electromagnetic interaction or attraction of the wheels 12 effected by the measuring unit relative to the pipeline 1 that must embodied to be ferromagnetic. As a result of the lightweight construction by use of fewer measuring and sensor units 3, the device is very flexible and adjustable to different diameters. The individual functional units 8 move across the wall and thus cause the central part 6 to rotate. The drive force directed in the direction of the central axis A of the pipeline 1 causes advancement along the pipeline.

The spring packs 18 can be configured as parts of a failsafe device. In an emergency situation, they can be pressed apart by means of suitable spring packs which causes expansion of the frame parts 28, also disk-shaped, along the center axis A of the device. With additional employment of an inflatable sealing sleeve, the device can be forcedly moved by means of media to be introduced at a remote location out of the pipeline or can be forcedly moved to a removal station.

The specification incorporates by reference the entire disclosure of German priority document 10 2007 058 043.8 having a filing date of Nov. 30, 2007.

While specific embodiments of the invention have been shown and described in detail to illustrate the inventive principles, it will be understood that the invention may be embodied otherwise without departing from such principles.

What is claimed is:

1. A device for nondestructive testing of pipelines, wherein the device is adapted to move along a pipeline, wherein the device comprises at least one measuring unit for acquiring measured data of the pipeline and wherein the device is self-propelled and has at least one functional unit rotatable about a central axis of the device, wherein the at least one functional unit performs at least one function selected from the group consisting of acquiring measured data and driving the device; wherein the device further comprises a frame that is variable in a direction along an axis that is perpendicular to a central axis of the device, wherein the at least one functional unit is arranged on the frame.

2. The device according to claim 1, further comprising an electric generator.

3. The device according to claim 1, wherein the at least one functional unit is rotatable about an axis perpendicular to the central axis of the device.

4. A device for nondestructive testing of pipelines, wherein the device is adapted to move along a pipeline, wherein the device comprises at least one measuring unit for acquiring measured data of the pipeline and wherein the device is self-propelled and has at least one functional unit rotatable about a central axis of the device, wherein the at least one functional unit performs at least one function selected from the group consisting of acquiring measured data and driving the device; wherein the at least one functional unit comprises a drive unit whose drive means are positionable at an angle to a perpendicular plane through a central axis of the device.

5. The device according to claim 4, wherein the drive means are electromotively driven wheels.

6. The device according to claim 1, wherein the at least one functional unit is configured to produce a magnetic field.

7. A device for nondestructive testing of pipelines, wherein the device is adapted to move along a pipeline, wherein the device comprises at least one measuring unit for acquiring measured data of the pipeline and wherein the device is self-propelled and has at least one functional unit rotatable about a central axis of the device, wherein the at least one functional unit performs at least one function selected from the group consisting of acquiring measured data and driving the device; wherein the at least one functional unit is configured to produce a magnetic field; wherein the at least one functional unit comprises a drive unit whose drive means are positionable at an angle to a perpendicular plane through a central axis of the device and wherein the drive means are configured to be forced against the pipe wall by magnetic interaction with the pipe wall.

8. The device according to claim 1, further comprising a device for electromechanical distance regulation.

9. The device according to claim 1, wherein the device is moved along the pipeline by electromagnetic interaction with the pipeline.

10. The device according to claim 1, wherein the at least one measuring unit measures by at least one of MFL, EMAT, EC and ultrasound.

11. The device according to claim 1, wherein the device is designed, despite the at least one functional unit that is rotatable, so as to be neutral with regard to counter torque relative to a central axis of the device.

12. A device for nondestructive testing of pipelines, wherein the device is adapted to move along a pipeline, wherein the device comprises at least one measuring unit for acquiring measured data of the pipeline and wherein the device is self-propelled and has at least one functional unit rotatable about a central axis of the device, wherein the at least one functional unit performs at least one function selected from the group consisting of acquiring measured data and driving the device; wherein the device further comprises a non-rotating tender.

13. The device according to claim 12, wherein the non-rotating tender has at least one guide means counteracting a rotational movement.

14. The device according to claim 1, wherein the device has spring force-loaded support elements.

15. A device for nondestructive testing of pipelines, wherein the device is adapted to move along a pipeline, wherein the device comprises at least one measuring unit for acquiring measured data of the pipeline and wherein the device is self-propelled and has at least one functional unit rotatable about a central axis of the device, wherein the at least one functional unit performs at least one function selected from the group consisting of acquiring measured data and driving the device; wherein the device further comprises a failsafe system.

16. The device according to claim 15, further comprising a folding sealing sleeve for sealing a pipeline cross-section in order to enable a device located in the pipeline to be moved out by a medium-based conveying action.

17. The device according to claim 1, further comprising a communication device configured to communicate by bidirectional, low-frequency signals.

18. The device according to claim 1, comprising several of said at least one functional unit, wherein the device is configured for complete pipe wall coverage by a combination of strips acquired by said several functional units while being rotated and advanced along the pipeline.

* * * * *